(12) United States Patent
Neri et al.

(10) Patent No.: US 6,310,643 B1
(45) Date of Patent: Oct. 30, 2001

(54) METHOD OF DETECTING ADHESIVE MATERIAL ON A BLANK FROM WHICH TO FORM A CONTAINER FOR TOBACCO ARTICLES

(75) Inventors: Armando Neri, Bologna; Stefano Chini, San Lazzaro Di Savena, both of (IT)

(73) Assignee: G.D Societa'per Azioni, Bologna (IT)

( * ) Notice: Subject to any disclaimer, the term of this patent is extended or adjusted under 35 U.S.C. 154(b) by 0 days.

(21) Appl. No.: 09/094,254

(22) Filed: Jun. 9, 1998

(30) Foreign Application Priority Data

Jun. 10, 1997 (IT) ............................................. BO97A0355

(51) Int. Cl.[7] ...................................................... H04N 7/18
(52) U.S. Cl. ............................................. 348/86; 382/141
(58) Field of Search ....................... 53/64, 466; 156/578; 206/86; 209/536; 348/86, 91–95; 382/141, 143; 493/29, 375, 438; H04N 7/18

(56) References Cited

U.S. PATENT DOCUMENTS

| | | | |
|---|---|---|---|
| 4,999,967 | * | 3/1991 | Hoffman ................................... 53/64 |
| 5,073,951 | * | 12/1991 | Hayashi ............................... 382/141 |
| 5,558,743 | * | 9/1996 | Focke et al. .......................... 156/578 |
| 5,716,313 | * | 2/1998 | Sigrist et al. ......................... 493/438 |
| 5,876,317 | * | 3/1999 | Sigrist et al. ........................... 493/29 |
| 5,877,506 | * | 3/1999 | Focke et al. .......................... 209/536 |
| 5,878,875 | * | 3/1999 | Leong .................................... 206/86 |
| 5,983,600 | * | 11/1999 | Heide et al. .......................... 493/375 |
| 5,992,494 | * | 11/1999 | Focke et al. .......................... 156/578 |
| 6,062,000 | * | 5/2000 | Focke et al. ............................ 53/466 |

FOREIGN PATENT DOCUMENTS

| | | |
|---|---|---|
| 2297616 A | 8/1996 | (GB) . |
| 07065805 | 3/1995 | (JP) . |
| 09105669 | 4/1997 | (JP) . |
| WO 9634273 A | 10/1996 | (WO) . |

* cited by examiner

Primary Examiner—Richard Lee
(74) Attorney, Agent, or Firm—Marshall, Gerstein & Borun

(57) ABSTRACT

A method of detecting adhesive material applied to a blank from which to form a container for tobacco articles, wherein the adhesive material forms at least one continuous mass of adhesive material on one face of the blank; the method providing for reproducing an image of at least one part of the face including a first portion corresponding to the face portion covered by the mass, and a second portion corresponding to the face portion free of the mass; electronically defining an application region in the image; and emitting a cover signal depending on the portion of the application region occupied by the first image portion.

3 Claims, 3 Drawing Sheets

METHOD OF DETECTING ADHESIVE MATERIAL ON A BLANK FROM WHICH TO FORM A CONTAINER FOR TOBACCO ARTICLES

BACKGROUND OF THE INVENTION

The present invention relates to a method of detecting adhesive material on a blank from which to form a container for tobacco articles.

In particular, the invention relates to a method of detecting adhesive material on a blank from which to form a hinged-lid packet of cigarettes, to which the following description refers purely by way of example.

Adhesive material is applied to cigarette packet blanks to join parts of the blank to one another, as well as to parts of a collar and to parts of a foil wrapping containing the cigarettes.

The adhesive material is applied by a gumming unit comprising a conveyor for feeding the blanks along a given path, and one or more gumming devices arranged along the path to apply the adhesive material to the blanks.

One commonly used type of gumming device comprises at least one gumming roller, which is positioned contacting adhesive material in a tank, and rolls along the blanks to deposit the adhesive material as the blanks are fed along the path.

Alternatively, adhesive material is applied by spray guns, which spray a quantity of adhesive material through nozzles as the blanks are fed past the guns.

Adhesive material is also applied to the blanks by means of spreading guns, which, like spray guns, dispense a controlled quantity of adhesive material through nozzles, but which, unlike spray gumming devices, is spread as opposed to being sprayed, onto the blanks.

The gumming unit provides for applying adhesive material to given portions of the blanks, and in sufficient quantities to ensure the packets formed from the blanks are stable.

The gumming devices described above do not always provide for applying the adhesive material correctly and in the right quantities to the given portions of the blanks. Which means the gumming must be checked to enable any improperly gummed blanks to be rejected immediately and prevented from being formed into packets, which will inevitably have to be rejected and opened to salvage the cigarettes inside. This is especially so when applying adhesive material using spray or spreading gun gumming units, the nozzles of which are subject to clogging, due to impurities in the adhesive material, or due to the adhesive material drying and hardening at the nozzle outlets.

One known method of eliminating the above drawbacks is to check the flow of adhesive material along a supply conduit common to a number of nozzles remains constant, or varies within predetermined limit values and in time with the passage of the blanks past the guns. Such a method, however, fails to meet current requirements, by failing to determine small variations in flow, and is especially inaccurate in the case of gumming units with a large number of nozzles.

Another known method is to check the flow of adhesive material through each nozzle by means of a sensor located along the conduit supplying the adhesive material to the nozzle or at the outlet of each nozzle. Though more effective, this solution complicates the design of the guns by requiring a flow sensor for each nozzle.

A further drawback of the above methods is that they fail to provide for determining whether the adhesive material is applied to the correct portion of the blank. That is, even if the flow of adhesive material indicates correct operation of the guns, there is no guarantee that the adhesive material has been applied at the right points. Moreover, methods based on measuring the flow of adhesive material cannot be applied when depositing adhesive material using the gumming rollers described previously.

From GB-A-2297616 it is known to check the masses of adhesive material applied to the blank in order to find whether the masses of adhesive material are applied in the correct position and cover a given length. According to the method referred above, a check is made in a comparison device between a predetermined linear pattern and a detected linear pattern, in case the two patterns do not coincide, the comparison device transmits an error signal.

This method, even though it has proved to be more reliable than the methods previously described, has the drawback that the comparison device, which acts on a strict coincidence between the predetermined pattern and the detected pattern, produces an error signal even when the masses adhesive material contain a sufficient quantity of adhesive material and are arranged in an acceptable position.

Moreover, the detection of glue masses is based on the difference between peaks of darkness and peaks of brightness, which are generated by inclined light beams impinging upon the blank and the glue masses. The glue masses are offset in respect of the flat blank and, for this reason generates shadows, which correspond to the peaks of darkness, and reflect part of the beams generating in this way the peaks of brightness. A blank from which to form a container for tobacco articles is provided with prescored lines along which the blank is folded. The prescored lines are offset in respect of the level of a flat blank in the same way as the masses of adhesive material applied on the blank itself, then the check method described in GB-A-2297616 is not suitable for checking the presence of glue on blanks from which to form a container for tobacco articles, because of the prescored lines.

SUMMARY OF THE INVENTION

It is an object of the present invention to provide a method of detecting adhesive material on blanks from which to form packets of cigarettes, and which provides for overcoming the aforementioned drawbacks.

According to the present invention, there is provided a method of detecting adhesive material applied to a blank from which to form a container for tobacco articles, the adhesive material forming at least one continuous mass of adhesive material on one face of the blank; and the method being characterized by comprising the steps of reproducing an image of at least one part of said face comprising a first image portion corresponding to a face portion covered by said mass, and a second image portion corresponding to a face portion free of said mass; electronically defining a given application region in said image; and emitting a cover signal depending on the portion of said application region occupied by said first image portion.

The method of the present invention is particularly advantageous in respect of the prior art because with only one signal, namely the cover signal, it is possible to acquired an information concerning the quantity of adhesive material contained in a mass and information relating to the position, in fact the control is made solely inside said given region and the cover signal is acquired solely inside said region.

Moreover, the cover signal is compared with a range of acceptability, which alone represent a level of acceptability of the position and the quantity of adhesive material.

BRIEF DESCRIPTION OF THE DRAWINGS

A non-limiting embodiment of the present invention will be described by way of example with reference to the accompanying drawings, in which.

DETAILED DESCRIPTION OF THE INVENTION

Figure 1:
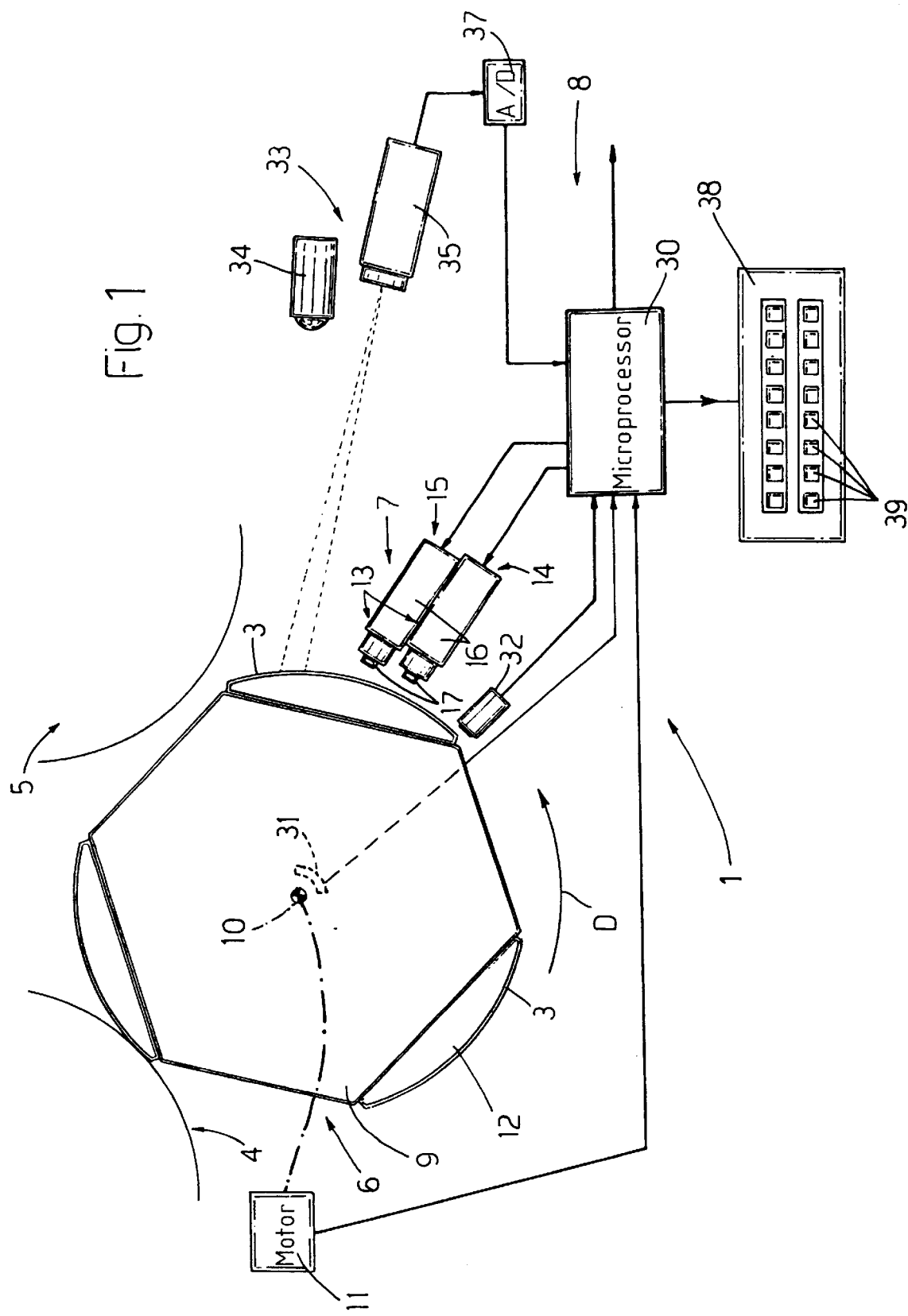
FIG. 1 shows a schematic side view, with parts removed for clarity, of a gumming unit implementing the method according to the invention.

Number 1 in FIG. 1 indicates a gumming unit for applying adhesive material 2 to blanks 3 from which to form known hinged-lid packets of cigarettes (not shown).

Gumming unit 1 is located between a supply unit 4 for supplying blanks 3, and a feed unit 5 for the gummed blanks 3, i.e. the blanks 3 to which adhesive material 2 has been applied, and comprises a conveyor 6, a spray gumming device 7, and a control unit 8.

Conveyor 6 comprises a drum 9, which is rotated anticlockwise in FIG. 1 about a respective axis 10 by a motor 11 to feed blanks 3 along a path P and in a given traveling direction D. Drum 9 has a number of plates 12 equally spaced about axis 10 and having known suction holes (not shown) for retaining a respective blank 3 on each plate 12.

Spray gumming device 7 is located along path P, and comprises a number of guns 13 arranged in two rows 14 and 15 extending crosswise to traveling direction D. Each gun 13 receives adhesive material 2 via a valve body 16 for metering adhesive material 2, and comprises a nozzle 17 for injecting measured quantities of adhesive material 2, which assume the form of drops 18 on blank 3.

Figure 2:
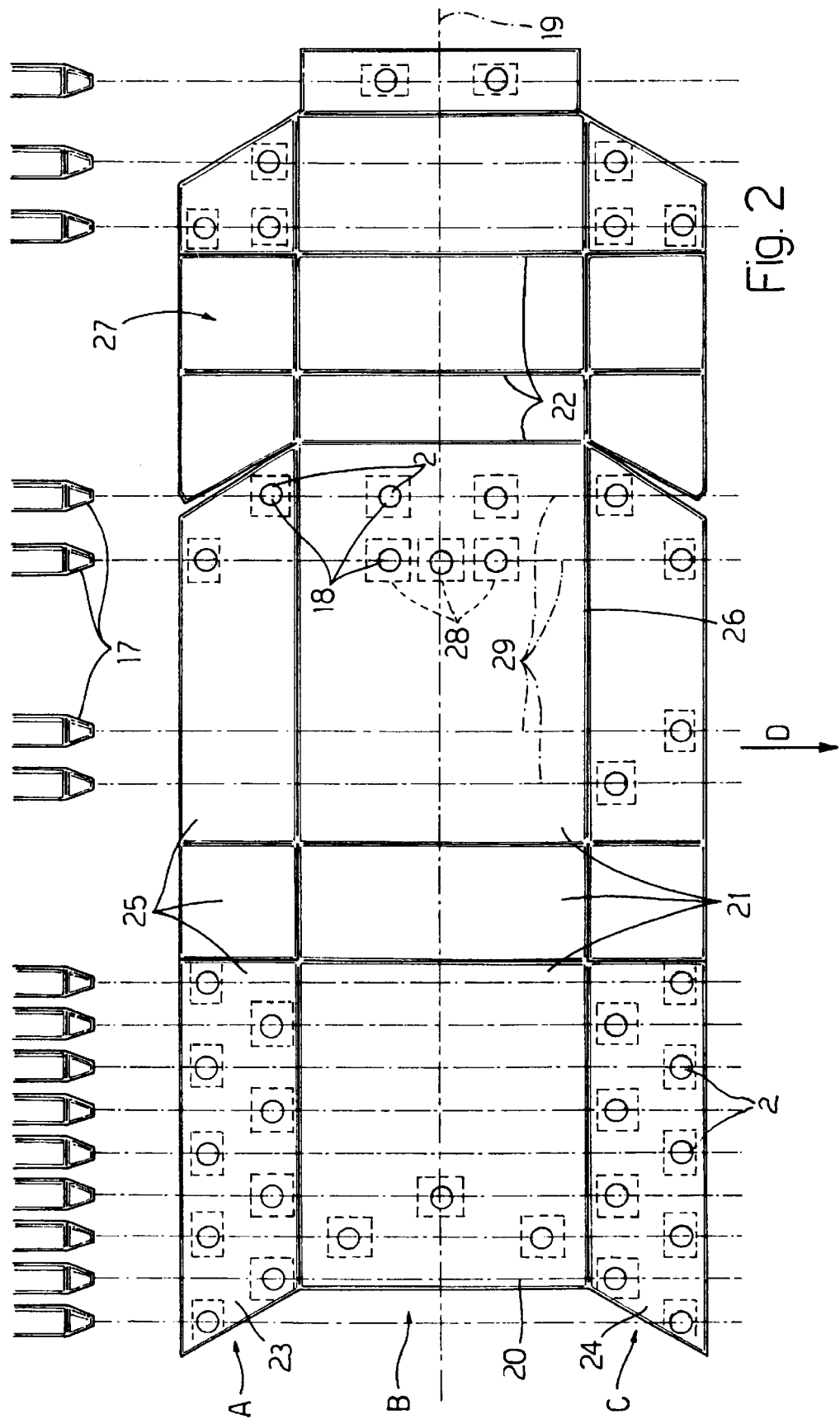
FIG. 2 shows a plan view of a blank gummed in the course of a gumming step.

With reference to FIG. 2, blank 3 has a longitudinal axis 19, and is divided into a central portion 20 comprising flat panels 21 separated from one another by transverse bend lines 22, and into two lateral portions 23 and 24, each comprising flat tabs 25 connected to central portion 20 along longitudinal bend lines 26.

Blank 3 has a relatively rough face 27, which eventually forms the inner surface of the cigarette packet (not shown), and on which are indicated by the dash lines in FIG. 2 a number of application regions 28 determined according to the acceptability of the location of drops 18 with respect to blank 3. That is, the location of each drop 18 is considered acceptable when drop 18 falls within a respective region 28.

The size of application regions 28 is determined according to the application precision required, which in turn varies according to the location of regions 28 with respect to blank 3. For example, drops 18 deposited close to the outer perimeter of blank 3 must be applied more accurately than those deposited on the central portion of blank 3, to prevent adhesive material 2 from oozing out when tabs 25 are brought into contact with one another and compress drops 18, thus increasing the surface of blank 3 coated with adhesive material 2 and possibly resulting in leakage of adhesive material 2.

Blanks 3 are fed along path P with respective longitudinal axes 19 perpendicular to traveling direction D, and the adhesive material 2 injected by guns 13 is deposited on blanks 3 in the form of drops 18 arranged along straight application lines 29 substantially perpendicular to longitudinal axis 19 and parallel to traveling direction D. FIG. 2 shows nozzles 17 of rows 14 and 15 of guns 13, and each nozzle 17 is aligned with a respective straight application line 29.

Control unit 8 comprises a microprocessor 30 to which are connected an encoder 31 for determining the angular position of plates 12 of conveyor 6 with respect to axis 10, and a sensor 32 located upstream from gumming device 7 and for determining the position of blank 3 on plate 12 of conveyor 6. Microprocessor 30 is connected to each gun 13 to control operation of respective valve body 16, and to motor 11 to arrest, if necessary, both injection of adhesive material 2 and rotation of drum 9.

Control unit 8 also comprises a detecting device 33 located along path P, immediately downstream from gumming device 7 in traveling direction D. Detecting device 33 in turn comprises a light source 34 for illuminating face 27 of blanks 3; and a television camera 35 located alongside light source 34 and for forming an analog image "IMA" of face 27.

Analog image "IMA" corresponds with a signal depending on the brightness of blank 3 and defined by a matrix of dots or so-called "pixels" 36, each of which is assigned an analog value "VA" depending on the brightness of the blank at pixel 36, and two coordinates "X" and "Y" depending on the location of pixel 36 in the image formed by camera 35.

The brightness of blank 3 varies according to the light reflected by face 27 and by drops 18 on face 27. That is, though normally light-coloured, relatively rough face 27 reflects less light than drops 18, which normally have a smooth surface and, regardless of the colour of adhesive material 2, reflect more light.

Camera 35 is connected to an analog-digital converter 37 for converting the analog values "VA" of pixels 36 into digital values "VD", and which is in turn connected to microprocessor 30 to transmit the digital values "VD" and the coordinates of pixels 36 to microprocessor 30 and so convert analog image "IMA" into a digital image "IMD".

Control unit 8 also comprises an indicator panel 38, which is connected to microprocessor 30 and in turn comprises a number of indicator lights 39, each indicating the operating state of a respective gun 13.

Figure 3:
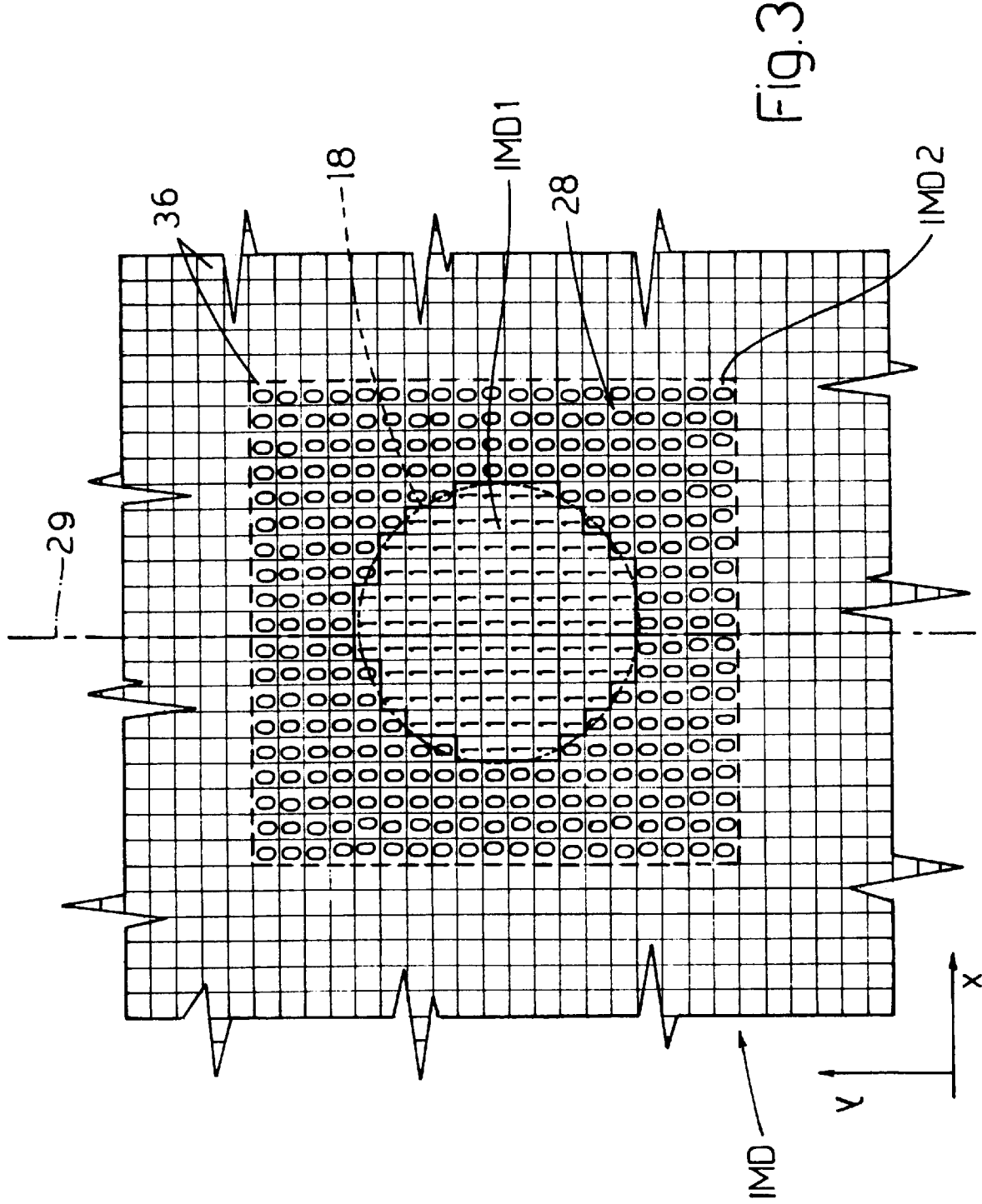
FIG. 3 shows a schematic electronic reproduction of a portion of the FIG. 2 blank.

The FIG. 3 portion of digital image "IMD". substantially corresponds to a given application region 28 of blank 3, and is represented by a set of pixels 36 in the form of small squares with respective "1" or "0" values and arranged in orderly manner along the "X" and "Y" coordinates. The values of pixels 36 represent digital values "VD", which, when equal to 1, indicate the presence, and, when equal to 0, indicate the absence of adhesive material 2 at the respective "X" and "Y" coordinates.

Each set of pixels 36 assigned digital values "VD" equal to 1 defines a respective image portion IMD1 corresponding to the part of blank 3 covered with adhesive material 2; and each set of pixels 36 assigned digital values "VD" equal to 0 defines an image portion IMD2 corresponding to the part of blank 3 free of adhesive material 2.

That is, as opposed to being shown on inner face 27 of blank 3, application regions 28 are simply created electronically on digital image "IMD" formed by camera 35, and are predefined in a memory of microprocessor 30 by memorizing given "X1" and "Y1" values of coordinates "X" and "Y".

In actual use, blanks 3 are transferred by supply unit 4 to drum 9, which feeds blanks 3 along path P and transfers the gummed blanks 3 to feed unit 5.

As drum 9 rotates, encoder 31 determines the angular position of drum 9 and plates 12, while sensor 32 determines the position of blank 3 on respective plate 12. The signals emitted by encoder 31 and sensor 32 are transmitted to microprocessor 30, which activates guns 13 independently of one another to apply drops 18 of adhesive material 2 to application regions 28. Adhesive material 2 is released according to the position of blank 3 with respect to nozzles 17.

When the gummed blank 3 is illuminated by light source 34, face 27 and respective drops 18 partly reflect the light towards camera 35, which detects the brightness of the various parts of blank 3. The analog image "IMA" signal, i.e. the respective analog values "VA" and "X" and "Y" coordinates of the relevant pixels 36, is transmitted to converter 37, which provides for converting analog values "VA" into digital values "VD".

In converter 37, each analog value "VA" is compared with a discriminating or threshold value "VS", and, whenever an analog value "VA" is greater than or equal to value "VS", the corresponding digital value "VD" is assigned a "1" value. Conversely, the digital value "VD" is assigned a "0" value. The digital values "VD" and the values of the "X" and "Y" coordinates of pixels 36 are transmitted to microprocessor 30, in which the "X1" and "Y1" values of the "X" and "Y" coordinates of each application region 28 of blank 3 have been set beforehand, and which contains a signal corresponding to a digitized image "IMD" of blank 3, and the "X1" and "Y1" values of the application regions 28 of blank 3.

Each pixel 36 assigned a "0" digital value "VD" forms part of image portion IMD2, and each pixel 36 assigned a "1" digital value "VD" forms part of one of portions IMD1.

The analog-digital conversion is preferably only performed for the analog values "VA" of pixels 36 in regions 28.

For each region 28, microprocessor 30 counts and adds the pixels 36 with "1" digital values "VD", the resulting sum representing the value of a cover signal "SR" relative to that particular region 28. That is, cover signal "SR" depends on the portion of application region 28 occupied by said first image portion "IMD 1".

Microprocessor 30 compares cover signal "SR" with a preset range of values "I", and, if the cover signal "SR" is outside the given range "I", emits an error signal "SE" to arrest gumming unit 1 (that is, to arrest motor 11 of drum 9 and guns 13).

Microprocessor 30 assigns each error signal "SE" an address signal "SI" defined by the mean values "X1M" and "Y1M" of the "X1" and "Y1" values of the "X" and "Y" coordinates of the region 28 causing the emission of error signal "SE", and activates light 39 indicating the operating state of the respective gun 13 responsible for applying adhesive material 2 to the region 28 corresponding to mean values "X1M" and "Y1M", the indicator light 39 to be activated being determined by means of address signal "SI".

As application regions 28 are arranged along straight application lines 29, each of which is aligned with a given gun 13, according to a variation, address signal "SI" is defined solely by mean value "X1M" of value "X1", which determines the location of straight application line 29 and therefore of the respective gun 13.

Besides preventing the supply of improperly gummed blanks 3, this therefore provides for rapidly determining the malfunctioning gun 13.

The method described is especially advantageous by only determining the presence of adhesive material 2 in application regions 28.

One way of using the method described, which is especially suitable for controlling the operating state of guns 13 when drum 9 is rotated at particularly high speed, is to check a small portion of each blank 3 as blanks 3 travel past detecting device 33, and vary the small check portion cyclically for successive blanks traveling past detecting device 33. That is, each blank 3 is divided theoretically into three portions "A", "B", "C" extending parallel to longitudinal axis 19 of blank 3 and corresponding, say, to portions 23, 20, 24 as shown in FIG. 2, and each of the three portions is examined singly every three successive blanks. This does of course mean not all of regions 28 are checked, and improperly gummed blanks 3 may be supplied to unit 5. Nevertheless, in the event of a nozzle 17 or a gun malfunctioning and going undetected, the malfunction is definitely detected when checking the next two blanks.

What is claimed is:

1. A method of detecting adhesive material (2) applied to a blank (3) from which to form a container for tobacco articles, said blank (3) having prescored lines along which the blank may be folded, the adhesive material (2) forming a number of distinct masses (18) of adhesive material (2) on one face (27) of the blank (3); the method comprising the steps of:

reproducing an image (IMD) of at least one part of said face (27) comprising a number of first image portions (IMD1) corresponding to a face (27) portion covered by said masses (18), and a second image portion (IMD2) corresponding to a face (27) portion free of said masses (18);

said image (IMD) is generated by a video camera (35) and is defined by a number of pixels (36), each of which is assigned a digital value (VD) and two coordinates (X, Y) depending on the location of the pixels (36) with respect to the image (IMD); the image (IMD) is a digital image obtained from an analog image (IMA) defined by a number of analog values (VA) assigned to the pixels (36); said analog values (VA) being emitted by said video camera (35) as a function of a characteristic brightness of each point on the face (27) of the blank (3);

electronically defining a number of given application regions (28) equal to the number of said given masses (18) in said image (IMD); said given application regions (28) corresponding to regions (28) of said blank (3) and each of said application regions (28) being determined according to a respective acceptability criteria, according to which the location of each of said masses (18) is acceptable when inside a respective region (28) and unacceptable when outside said respective region (28) and said acceptability criteria for given masses (18) within the region (28) being defined by a given acceptable range of coverage values (I) extending from a minimum quantity of masses (18) in said region (28) sufficient to join parts of the blank to one another to a maximum quantity of masses (18) to prevent said masses (18) from oozing out of the blank when the parts are joined;

converting each analog value (VA) assigned to each pixel (36) in a given application region (28) into a digital value (VD) of 1 or 0, depending on whether said analog value (VA) is respectively above or below a given threshold value (VS);

determining within each of said application regions (28) the sum of the number of pixels (36) assigned a digital value (VD) of 1; said sum representing the value of a cover signal (SR) for said given application region (28);

emitting said cover signal (SR) for each region 28, the cover signal (SR) corresponding to the portion of said application region (28) occupied by a respective first image portion (IMD1) and thereby defining the quantity of each of said masses (18) inside the respective region (28);

comparing the cover signal (SR) of each respective region (28) with the given acceptable range of coverage values (I) for the respective regions (28); and emitting an error signal (SE) when at least one cover signal (SR) associated with a respective region (28 is outside said maximum quantity of said given acceptable range of coverage values (I).

2. A method as claimed in claim 1, wherein the face (27) of the blank (3) is illuminated by a light source (34) located alongside the video camera (35).

3. A method as claimed in claim 1, further comprising the step of assigning the cover signal (SI) defined by at least one mean value (X1M; Y1M) of the values (X1; Y1) of the coordinates (X; Y) characteristic of the application region (28).

* * * * *